United States Patent
Liang et al.

(10) Patent No.: US 8,536,326 B2
(45) Date of Patent: Sep. 17, 2013

(54) METHOD FOR PREPARING SUCRALOSE WITH HIGH YIELD

(75) Inventors: Hengbo Liang, Hubei Province (CN); Zhengyou Wang, Hubei Province (CN); Li Rao, Hubei Province (CN)

(73) Assignee: Hubei Yitai Pharmaceutical Co., Ltd., Hubei Province (CN)

( * ) Notice: Subject to any disclaimer, the term of this patent is extended or adjusted under 35 U.S.C. 154(b) by 37 days.

(21) Appl. No.: 13/008,920

(22) Filed: Jan. 19, 2011

(65) Prior Publication Data

US 2012/0184729 A1 Jul. 19, 2012

(51) Int. Cl.
*C13K 13/00* (2006.01)
*C07H 5/02* (2006.01)

(52) U.S. Cl.
USPC ....... 536/123.13; 536/122; 536/127; 536/4.1; 514/53

(58) Field of Classification Search
USPC ................ 536/123.13, 122, 127, 4.1; 514/53
See application file for complete search history.

(56) References Cited

FOREIGN PATENT DOCUMENTS

CN 101812095 A * 8/2010

OTHER PUBLICATIONS

Chen et al.; CN 101812095 A; Aug. 25, 2010 (Machine English Translation).*

* cited by examiner

*Primary Examiner* — Shaojia Anna Jiang
*Assistant Examiner* — Michael C Henry

(57) ABSTRACT

A method for preparing sucralose with high yield, comprising the following preparation steps: First, negative effects of other impurities on reaction are reduced by first preparing a pure Vilsmeier chlorinating reagent. Second, side reactions are prevented by adding composite catalyst to increase selectivity of chlorination reaction. Third, by extracting less polar impurities using less polar solvent when sucralose-6-ester is undergoing deesterification, products are qualified at the very first time so that refining steps are avoided. Accordingly, product loss is reduced and product yield is increased. By using the present invention to prepare sucralose, product yield could be increased to more than 40%.

7 Claims, No Drawings

METHOD FOR PREPARING SUCRALOSE WITH HIGH YIELD

BACKGROUND OF THE INVENTION

The present invention relates generally to pharmaceutical preparation and more specifically relates to a method for preparing sucralose.

There are many patented technologies worldwide for preparing sucralose from sucrose. However, product yield is low in general due to numerous defects in the course of preparation. The first defect is that by-products such as sulfur dioxide and the like are not well removed during preparation of a chlorinating agent. These acidic impurities seriously affect the selectivity of chlorination reaction and increase the quantity of oxidation products and carbonation products. As a result, product yield could not be increased. The second defect is that an effective catalyst is not available for increasing reaction selectivity. As a result of numerous experiments over a long period of time, the inventor of the present invention discovered that by adding a mixture of phenolic antioxidant and general phase transfer catalyst mixed according to a certain proportion in a reaction system, selectivity of chlorination reaction could be significantly increased, reaction temperature could be lowered, various side reactions could be reduced and product yield could be increased accordingly. The third defect is that sucralose-6-ester must undergo multiple refining steps during deesterification in order to produce qualified products, therefore product loss is increased and product yield is lowered. In view of the above, the inventor of the present invention extracts less polar impurities by using solvent so as to avoid loss and trouble as a result of multiple refining steps. Preparation of sucralose by using the method according to the present invention could increase product yield to more than 40%.

BRIEF SUMMARY OF THE INVENTION

In view of the aforesaid disadvantages now present in the prior art, the object of the present invention is to provide a method for preparing sucralose with high yield.

The technical proposal of the present invention is achieved as follows: First, add a chlorinating agent or a chlorinating agent solution dropwise to a mixed solvent composing of a fixed amount of DMF (N,N-dimethylformamide) and a removing agent; next, heat it up to a temperature ranging from 40 to 80° C. for reaction for a period ranging from 1 to 5 hours; then reduce pressure to evaporate the removing agent and obtain a pure Vilsmeier chlorinating reagent; then, add thereto a fixed amount of DMF and composite catalyst and cool it down to 0° C. and thereafter add dropwise thereto sucrose-6-acetic ester DMF solution; after that, heat it up gradually to a temperature ranging from 105 to 115° C. and maintain the temperature for a period ranging from 2 to 3 hours; next, cool it down to room temperature and neutralize it with alkali and extract it with an extracting agent; then, remove the extracting agent by vacuum removal, add water to dissolve it and cool it down for crystallization and thereby obtaining a crude product of sucralose-6-acetic ester; re-crystallize the crude product with water, ethyl acetate and so forth to obtain white sucralose-6-acetic ester crystals; after that, dissolve the crystals with methanol and then add dropwise thereto potassium hydroxide methanol solution until pH value reaches a range of 9 to 11; react for a period ranging from 3 to 5 hours and neutralize with diluted acetic acid, hydrochloric acid and so forth; next, reduce pressure to remove the solvent and then add water thereto for dissolution; after that, add thereto less polar extracting solvent to extract less polar impurities; after a majority of solvent is removed by reducing aqueous phase pressure, reduce temperature for crystallization and thereby obtaining an end product having a content of over 99% sucralose.

The chlorinating agent is any one of chloride sulfone, trichloromethyl chlorocarbonate or bis(trichloromethy)carbonate.

The removing agent is ethyl acetate, benzene, methylbenzene or cyclohexane.

The composite catalyst is composed of antioxidant and phase transfer catalyst.

The composite catalyst is composed of phenolic antioxidant and general phase transfer catalyst.

The less polar extracting solvent is chloroform, dichloroethane, trichloroethane, ethyl acetate or butyl acetate etc.

The advantages of the present invention are as follows:

First, negative effects of other impurities on reaction can be reduced by first preparing a pure Vilsmeier chlorinating reagent. Second, side reactions are prevented by adding composite catalyst to increase selectivity of chlorination reaction. Third, by extracting less polar impurities using less polar solvent when sucralose-6-ester is undergoing deesterification, products are qualified at the very first time so that refining steps are avoided. Accordingly, product loss is reduced and product yield is increased. By using the present invention to prepare sucralose, product yield could be increased to more than 40%.

DETAILED DESCRIPTION OF THE INVENTION

Two embodiments of the present invention are described below but the present invention is not limited to the described embodiments:

Embodiment 1

In room temperature, add 100 g of chloride sulfone dropwise to a solution composing of 100 ml of DMF, 100 ml of ethyl acetate and 1 g of composite catalyst. Next, heat it up to 65° C. and maintain the temperature for reaction for 3 hours, and then evaporate to dryness in vacuum. Next, add thereto 300 ml of DMF, control its internal temperature at a level not exceeding 5° C. and add dropwise thereto sucrose-6-ester DMF solution (containing 50 g of sucrose-6-ester). After that, heat it up gradually to 106° C. and maintain the temperature for reaction for 120 minutes. Next, cool down the reaction solution to room temperature and adjust its pH value to 7 with liquid caustic soda and then extract it with ethyl acetate for 4 times (4×200 ml) until there is no product in aqueous phase. Then, reduce pressure to remove solvent to obtain syrup substance. After that, add water to dissolve it and cool it down for crystallization and thereby obtaining a crude product which is weighed 44 g after drying. Re-crystallize the crude product with water and ethyl acetate to obtain 30.2 g of crystals with a content of 96% pure white sucralose-6-acetate. After that, dissolve the crystals with methanol and then add dropwise thereto potassium hydroxide methanol solution until pH value reaches a range of 9 to 11. React for a period ranging from 3 to 5 hours and then neutralize with diluted acetic acid. Next, reduce pressure to remove the solvent and then add water thereto for dissolution. After that, add thereto ethyl acetate to extract less polar impurities. After a majority of solvent is removed by reducing aqueous phase pressure, reduce temperature for crystallization and thereby obtaining 22 g of end product with a content of 99.2% sucralose.

Embodiment 2

In room temperature, add 100 g of chloride sulfone dropwise into a solution composing of 100 ml of DMF, 100 ml of methylbenzene and 1 g of composite catalyst. Next, heat it up to 65° C. and maintain the temperature for reaction for 3 hours, and then evaporate to dryness in vacuum. Next, add thereto 300 ml of DMF, control its internal temperature at a level not exceeding 5° C. and add dropwise thereto sucrose-6-ester DMF solution (containing 50 g of sucrose-6-ester). After that, heat it up gradually to 110° C. and maintain the temperature for reaction for 120 minutes. Next, cool down the reaction solution to room temperature and adjust its pH value to 7 with liquid caustic soda and then extract it with ethyl acetate for 4 times (4×200 ml) until there is no product in aqueous phase. Then, reduce pressure to remove solvent to obtain syrup substance. After that, add water to dissolve it and cool it down for crystallization and thereby obtaining a crude product which is weighed 42.8 g after drying. Re-crystallize the crude product with water and ethyl acetate to obtain 29.5 g of crystals with a content of 97% pure white sucralose-6-acetate. After that, dissolve the crystals with methanol and then add dropwise thereto potassium hydroxide methanol solution until pH value reaches a range of 9 to 11. React for a period ranging from 3 to 5 hours and then neutralize with diluted acetic acid. Next, reduce pressure to remove the solvent and then add water thereto for dissolution. After that, add thereto dichloromethane to extract less polar impurities. After a majority of solvent is removed by reducing aqueous phase pressure, reduce temperature for crystallization and thereby obtaining 21.5 g of end product with a content of 99.5% sucralose.

In spite of the above detailed description of the embodiments of the present invention, it is obvious that partial modifications and changes could be made by a person skilled in the art on the premise that they are not contrary to the present invention. Contents of the above description serve the purpose of descriptive illustrations only and do not serve to limit the present invention. Any method for preparing sucralose with high yield provided with the technical characteristics as mentioned in the above description should fall into the scope of the present prevention.

What is claimed is:

1. A method for preparing sucralose comprising:
   adding a chlorinating agent or a chlorinating agent solution dropwise to a mixed solvent composing of a fixed amount of DMF (N,N-dimethylformamide) and an impurities removing agent to obtain a first composition;
   heating the first composition up to a temperature ranging from 40 to 80° C. for reaction for a period ranging from 1 to 5 hours;
   evaporating the impurities removing agent from the first composition by reducing pressure of the first composition, thereby obtaining a pure Vilsmeier chlorinating reagent;
   adding DMF and composite catalyst to the pure Vilsmeier chlorinating reagent to obtain a second composition and cooling the second composition down to 0° C.;
   adding sucrose-6-acetic ester DMF solution dropwise to the second composition;
   heating the second composition up gradually to a temperature ranging from 105 to 115° C. and maintaining the temperature for a period ranging from 2 to 3 hours;
   cooling the second composition down to room temperature and neutralize the second composition with alkali to obtain a neutralized composition and extract the neutralized composition with an extracting agent;
   removing the extracting agent by vacuum removal to obtain a third composition;
   adding water to dissolve the third composition to obtain a fourth composition;
   cooling the fourth composition down for crystallization and thereby obtaining a crude product of sucralose-6-acetic ester;
   recrystallizing the crude product with water and ethyl acetate to obtain white sucralose-6-acetic ester crystals;
   dissolving the crystals with methanol to obtain a methanol solution;
   adding potassium hydroxide to the methanol solution until pH value reaches a range of 9 to 11 to obtain a fifth composition;
   leaving the fifth composition for reaction for a period ranging from 3 to 5 hours
   neutralizing the fifth composition with diluted acetic acid, hydrochloric acid and so forth;
   removing the solvent from the fifth composition by reducing pressure of the fifth composition to obtain a sixth composition;
   adding water to the sixth composition for dissolution;
   adding less polar extracting solvent to the sixth composition to extract less polar impurities;
   after a majority of solvent is removed by reducing aqueous phase pressure, reducing temperature for crystallization and thereby obtaining an end product having a content of more than 99% sucralose.

2. The method for preparing sucralose as in claim 1, characterized in that the chlorinating agent is chloride sulfone or trichioromethyl chlorocarbonate or bis(trichloromethyl)carbonate.

3. The method for preparing sucralose as in claim 1, characterized in that the impurities removing agent is ethyl acetate or benzene or methylbenzene or cyclohexane.

4. The method for preparing sucralose as in claim 1, characterized in that the composite catalyst is composed of antioxidant and phase transfer catalyst.

5. The method for preparing sucralose as in claim 1, characterized in that the said composite catalyst is composed of phenolic antioxidant and general phase transfer catalyst.

6. The method for preparing sucralose as in claim 1, characterized in that the less polar extracting solvent is, chloroform or dichloroethane or trichloroethane or ethyl acetate or butyl acetate.

7. The method for preparing sucralose as in claim 4, characterized in that the said composite catalyst is composed of phenolic antioxidant and general phase transfer catalyst.

* * * * *